United States Patent
Reminiac et al.

(10) Patent No.: US 7,582,874 B2
(45) Date of Patent: Sep. 1, 2009

(54) PROBE FOR MEASURING LIGHT IN A LIQUID, PROBE FOR DETECTING THE FLOCCULATION THRESHOLD OF A COLLOIDAL MEDIUM, RELATED DETECTION METHOD AND USE FOR DETERMINING THE FLOCCULATION OF ASPHALTENES

(75) Inventors: Myriam Reminiac, Le Havre (FR); Coralie Simonet, Le Havre (FR); André Diot, Fleurier (CH)

(73) Assignee: Total France, Puteaux (FR)

( * ) Notice: Subject to any disclaimer, the term of this patent is extended or adjusted under 35 U.S.C. 154(b) by 0 days.

(21) Appl. No.: 11/569,352

(22) PCT Filed: May 17, 2005

(86) PCT No.: PCT/FR2005/001231

§ 371 (c)(1),
(2), (4) Date: May 23, 2007

(87) PCT Pub. No.: WO2005/124312

PCT Pub. Date: Dec. 29, 2005

(65) Prior Publication Data

US 2008/0043240 A1 Feb. 21, 2008

(30) Foreign Application Priority Data

May 18, 2004 (FR) .................................. 04 05406

(51) Int. Cl.
*G01N 21/59* (2006.01)
(52) U.S. Cl. .................................................. 250/341.2
(58) Field of Classification Search ............... 250/341.2
See application file for complete search history.

(56) References Cited

U.S. PATENT DOCUMENTS

| | | | |
|---|---|---|---|
| 4,040,743 A | 8/1977 | Villaume et al. | |
| 4,628,204 A | 12/1986 | Maes | |
| 4,940,900 A * | 7/1990 | Lambert | 250/343 |
| 5,051,551 A * | 9/1991 | Doyle | 250/341.2 |
| 5,708,273 A * | 1/1998 | VonBargen | 250/341.2 |
| 5,973,779 A | 10/1999 | Ansari et al. | |
| 6,137,108 A * | 10/2000 | DeThomas et al. | 250/339.07 |
| 6,469,787 B1 | 10/2002 | Meyer et al. | |
| 2004/0011965 A1 | 1/2004 | Hodgkinson | |

FOREIGN PATENT DOCUMENTS

| | | |
|---|---|---|
| DE | 101 49 879 | 4/2003 |
| EP | 0 582 320 A2 | 2/1994 |
| JP | 11311602 A * | 11/1999 |
| WO | WO-2005/040482 | 5/2005 |

* cited by examiner

*Primary Examiner*—Constantine Hannaher
(74) *Attorney, Agent, or Firm*—Hirsch Simpson LLC

(57) ABSTRACT

The device measures a light in a liquid by introducing in the liquid at least one emitting probe. The emitting probe includes a transmitter connected to a first waveguide, a second waveguide, and included in the second waveguide, at least one reflecting surface. The device may be used in a method for measuring the flocculation threshold of a colloidal medium by gradually adding apolar solvent. The method includes a step which of determining, using at least one probe of the device, flocculation after adding amount of apolar solvent required for flocculation. The method is applicable to asphaltenes. The device may be used for measuring physicochemical properties in opaque media.

16 Claims, 1 Drawing Sheet

PROBE FOR MEASURING LIGHT IN A LIQUID, PROBE FOR DETECTING THE FLOCCULATION THRESHOLD OF A COLLOIDAL MEDIUM, RELATED DETECTION METHOD AND USE FOR DETERMINING THE FLOCCULATION OF ASPHALTENES

TECHNICAL FIELD

The subject of the invention is a novel method for detecting the flocculation of asphaltenes as well as a related detection probe for measuring light in heavy hydrocarbon products, waste oil, polluted water or any product containing an emulsion and, in particular, for measuring the flocculation threshold of a colloidal medium.

STATE OF THE ART

Petroleum products, and in particular fuel oils or residues from the distillation of petroleum, generally called "Black products" (Black oils) in the industry, are colloidal systems constituted by asphaltenes—i.e. very aromatic heavy molecules having paraffinic side chains—which are dispersed (or also said to be "peptized") in the form of micelles in an oil phase. These colloidal systems can be destabilized more or less easily, for example by thermal cracking or by dilution. Thus, in a refinery, the conversion method, called viscosity breaking (visbreaking), can lead to a precipitation of the asphaltenes as a result of the high temperatures of the method (generally higher than 400° C.). Likewise, the constitution of mixtures containing such colloidal systems can cause a precipitation of these asphaltenes by flocculation, in particular if the dilution environment is of the paraffinic type.

It is therefore necessary to know or to estimate the characteristics of these asphaltenes in black products, such as a petroleum product or a mixture of hydrocarbon products, in order to evaluate its inherent stability as well as its associated stability reserve. In fact, the greater the stability reserve the less the black product is subject to problems of precipitation of asphaltenes, or of compatibility by dilution with other chemical species, in particular paraffinic bases.

It will be noted that fuel oils or petroleum residues are constituted by a malthenic matrix (resins+paraffins) and asphaltenes dispersed in a colloidal form. The asphaltenes which have a very aromatic character (polar molecules) are insoluble in paraffins (apolar molecules). In order for a residue to be stable the asphaltenes must be maintained in suspension (or dispersed or peptized) in the oil matrix. The peptization of the asphaltenes is ensured by the resins which have both an aromatic character and an apolar character. When a residue has been destabilized, the asphaltenes flocculate aggregating together in the form of large particles which can cause blockages in filters present in the different treatment units or also cause damage to the metallurgy, for example the pipework.

The characteristic known as the value P, or inherent stability, for example of a black product, is defined in the industry by the following expression:

$P$=aromaticity of the malthenes/aromaticity of the asphaltenes, or $P=Po/(1-Pa)$, in which, Po represents the ability of the medium to solubilize asphaltenes, i.e. the aromatic character of the medium. The more aromatic this is the greater the Po is.

Pa is the aromatic character of the asphaltenes.

1−Pa represents the aromaticity of the medium necessary for solubilizing the asphaltenes present.

If P>1, the asphaltenes are peptized and are therefore stable. P−1 represents the stability reserve (the greater this reserve the less the black product is subject to problems of precipitation or compatibility).

The severity of a thermal shock such as that produced by a distillation or a visbreaking directly effects the aromaticity of the asphaltenes because the thermal cracking causes the detachment of the alkylated chains and the condensation of the asphaltenes. The asphaltenes which are more condensed and less branched (weaker Pa) will require a stronger solvent in order to remain dispersed. Thus, knowledge of the value of P, associated with that of Pa makes it possible to specify the settings for the operating conditions of the unit concerned so that it is operated without risk of precipitation of the asphaltenes, and consequently to satisfy the various requirements of the operator in terms of quality.

Moreover, knowledge of the solvent power values Po and of the aromatic character of the asphaltenes Pa is necessary in order to optimize the mixture of the different constituents of fuel oils. Thus if a flux (product capable of reducing the viscosity of a mixture) with a weak solvent power is added to a black product, for example visbroken, and having high Po and low Pa values, the value of the Po of the mixture is reduced which can lead to a destabilization of the black product, and consequently to flocculation of the asphaltenes because the resulting Po and Pa values are too low to satisfy the relationship P>1, i.e. the condition required for said asphaltenes to be peptized and therefore stable.

Conventionally the values of P and Pa, and then by calculation Po, of a black product are determined in the laboratory by a dilution in stages using a paraffinic solvent of said black product previously mixed with an aromatic solvent. The moment when flocculation occurs is recorded. The measurement is repeated for at least one other mixture with a different dilution rate. Results are thus obtained which make it possible by linear correlation to obtain the desired values of P and Pa and then to calculate Po from them.

In an experimental fashion the flocculation threshold in a given mixture can be detected by means of several optical probes operating in the infrared (IR) or the near infrared (NIR).

For example, the technique described in the patents FR-A-2 596 522 or U.S. Pat. No. 4,628,204 of Texaco Belgium SA, allows the measurement by IR of the flocculation threshold of a colloidal solution during its dilution. This measurement requires the correct choice in advance of the optical measuring probe (there are several probes) as a function of the nature and in particular of the magnitude of the presence of asphaltenes in the black product to be tested. In the event of a bad choice by the operator it is then necessary to carry out cleaning of the equipment, then to prepare the sample again for another measurement with another probe which leads to a waste of time which can be greater than one hour of operator time while the duration of an analysis is approximately 1 hour 30 minutes to 2 hours, in particular if the choice of a different probe proves to be judicious.

Another example is the method developed by Shell in collaboration with its Dutch partner Zematra, a manufacturer of analytical apparatuses. This method, in which the detection of the flocculation threshold of the colloidal medium is carried out using a single probe, constituted by a single optical fibre surrounded by glass, unfortunately cannot be used for the whole range of black products. In fact, the systematic heating of the sample at 150° C., aside from the safety problems, can cause, for certain types of black products, degradations which are detrimental to the measurement of the flocculation threshold. As regards the duration of an analysis it is relatively long because it can be greater than 5 hours.

Another method is also proposed for measuring the value of P in black products with a "Porla" apparatus manufactured by the Finnish company FMS (Finnish Measurement Systems Ltd), and marketed by the English company Med-Lab. This apparatus uses a measuring cell with continuous circulation of the sample to be analyzed with an optical detection of the flocculation threshold by means of a prism operating in total reflection. The measurement range is very wide and a result can always be obtained even with black products the flocculation threshold of which is reputed to be difficult to measure. However, these results are obtained after modifications to the operating parameters of the method which are then a function of the nature of the product, which is unacceptable when the range of products to be analyzed is very variable, as in the petroleum industry.

The methods currently proposed for measuring the flocculation threshold of asphaltenes in hydrocarbon products therefore have a certain number of drawbacks. They do not necessarily provide the required simplicity, rapidity and precision of results, in particular for an effective continuous control of a treatment unit, for example for visbreaking, and/or a mixing unit. Nor do they allow the direct analysis of a wide range of products according to their asphaltene content. They use techniques which are not easily automated and/or which are not very simple to use.

The present invention aims to remedy one or more of the drawbacks mentioned above.

SUMMARY OF THE INVENTION

The subject of the invention is a device for measuring light in a liquid by inserting into said medium at least one probe comprising:

an emitter connected to a first waveguide emitting at the level of a detection zone a light beam directly onto said zone, a second waveguide receiving in a perpendicular manner said light beam sent back to a receiver for analysis; and included in this second waveguide, at least one surface for reflecting the light beam by rotation or by reflection, situated downstream of said detection zone.

According to one embodiment, the light is constituted by wavelengths belonging to the spectral range of the near infrared or the infrared.

According to one embodiment, the reflecting surface is constituted by a mirror.

According to one embodiment, the device is suitable for measuring the flocculation threshold of a colloidal medium and comprises at least one probe operating in indirect transmission by reflection.

According to one embodiment, the device also comprises a probe operating in direct transmission.

According to one embodiment, said at least one probe comprises an emitter connected to a first waveguide emitting at the level of a detection zone of the medium, reflecting mirrors downstream of said detection zone at the aperture and a second waveguide connected to a receiver.

According to one embodiment, the reflecting mirrors operate at 180°.

According to one embodiment, the reflecting mirrors and the second waveguide are integrated in a single piece.

According to one embodiment, the device comprises two probes and the second waveguides are merged.

According to one embodiment, the first and second waveguides are made of glass.

According to one embodiment, the device comprises two probes operating in indirect transmission by reflection, these probes operating at the level of detection zones of the medium with distinct dimensions.

According to one embodiment, the device comprises a probe operating in indirect transmission by reflection, this probe operating at the level of a detection zone of the medium the dimension of which is variable.

According to one embodiment, the device comprises on the one hand a first probe operating in direct transmission and operating at the level of a first detection zone of the medium; and on the other hand two probes operating at the level of detection zones of the medium with distinct dimensions, these three zones having increasing dimensions, the first detection zone of the probe operating in direct transmission having the smallest dimension.

The subject of the invention is also, independently, a device for measuring the flocculation threshold of a colloidal medium comprising at least one probe, operating in indirect transmission by reflection. The above device is particularly suited to this use.

The subject of the invention is also a method for measuring the flocculation threshold of a colloidal medium by the addition in stages of apolar solvent using the device according to the invention, comprising the stage of determination, using at least one probe of said device, of flocculation after addition of the quantity of apolar solvent necessary for flocculation.

The subject of the invention is also a method for measuring the flocculation threshold of a colloidal medium by the addition in stages of apolar solvent comprising the following stages: (i) at least two probes are introduced into the medium operating at the level of detection zones with distinct dimensions; (ii) which of the two probes is suitable for the measurement is determined by determination of the transmission threshold of the medium before the addition of apolar solvent; and (iii) using the thus-designated probe flocculation is determined after addition of the quantity of apolar solvent necessary for flocculation.

According to one embodiment, the probes are probes emitting in the NIR range and the flocculation occurrence is determined by determination of the absorption peak.

According to one embodiment, said at least two probes are contained in the device according to the above invention.

According to one embodiment, the measuring probe is chosen automatically from at least two probes.

According to one embodiment, the method is carried out at ambient temperature.

According to one embodiment, the medium comprises asphaltenes.

The subject of the invention is also a method for determining the stability of a mixture comprising asphaltenes by successively implementing at least twice the method according to the above invention on a medium containing the mixture and a given quantity of aromatic solvent, at different dilution rates.

According to one embodiment, the aromatic solvent/paraffinic solvent pair used is the toluene/n-heptane pair.

Finally, the invention relates to the use of the device according to the invention for measuring physico-chemical characteristics in opaque media, such as heavy hydrocarbons, waste oil, polluted water and emulsions.

DETAILED DESCRIPTION OF THE EMBODIMENTS OF THE INVENTION

Figure 1:
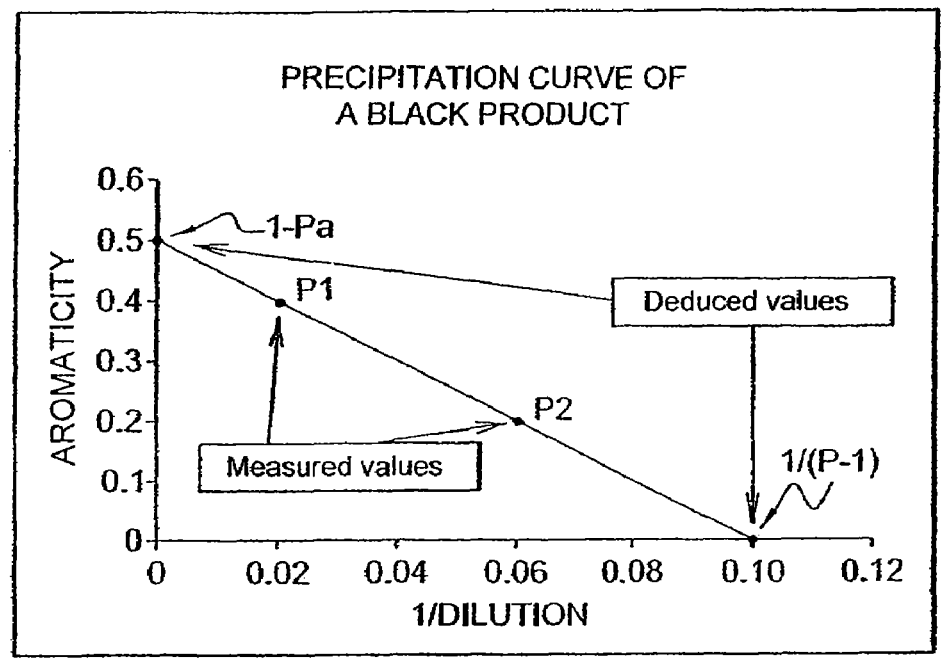
FIG. 1 is a representation of a graph of the aromaticity of the solvent as a function of the reciprocal of the dilution, i.e. the precipitation curve of a black product which, at a determined dilution rate of this same black product, shows the minimum aromaticity of the solvent required so that the mixture does not precipitate.

With reference to FIG. 1, the method using the standard probes proposed by Texaco Belgium SA are described for the determination of the values of P, Po and Pa, for a given mixture of black product.

The inherent stability of any colloidal system is quantified by a dilution using a paraffinic solvent of a black product, such as a fuel oil, a residue from the atmospheric distillation of petroleum (or under vacuum), a crude oil, previously mixed with an aromatic solvent. This inherent stability (P) depends on the aromatic character of the asphaltenes (Pa) and on the aromatic character of the medium (Po), as was described above. Thus the inherent stability P of a colloidal system is determined by measuring the flocculation threshold of at least 2 different mixtures. Starting from at least these 2 points, a straight line is plotted, called the precipitation of a black product (FIG. 1), which makes it possible to obtain the parameters Pa and P, and then by calculation the value Po.

By the addition of a paraffinic solvent into the black product, the mixture becomes unstable starting from a certain dilution rate called the "minimal dilution rate".

The following definitions are used:
Dilution rate (ml/g):
total volume of solvent (aromatic+paraffinic) in millilitres/mass of black product in grams.
inherent stability P of the black product:
P=1+Minimal dilution rate. Here we find the concept of P−1 as stability reserve.

For the experimental measurements, two types of solvents are used, the first is binary, essentially constituted by aromatic molecules for the dilution of the sample (for example toluene, xylene, or also 1-methylnaphthalene) and the second is apolar of the paraffinic solvent type (for example n-heptane, cetane, or also isooctane) in order to produce flocculation of the asphaltenes.

The aromaticity of the binary solvent is defined as follows:
volume of aromatic solvent/volume of total solvent. The value 1−Pa is equal to the limit aromaticity of the binary solvent allowing the stability of the mixture to be maintained.

In the case of strong aromaticities of the solvent, the mixture remains stable. In the case of weak aromaticities of the solvent, the mixture becomes unstable. A limit aromaticity of the solvent therefore exists allowing the stability of the mixture to be maintained.

The aromatic character of the asphaltenes is defined by:
Pa=1−limit aromaticity
The function which, at a given dilution rate of the black product, shows the minimum aromaticity of the solvent in order for the mixture not to precipitate, is called the precipitation curve. The equation of the precipitation curve is given by the formula:

Aromaticity of the solvent as a function of the dilution rate, or in this case:

$$1-Pa = f(1/\text{dilution rate}) = A + B/\text{dilution rate}.$$

A and B are constants which depend solely on the sample and make it possible to obtain the values of P, Po and Pa.

The procedure is as follows. A first mixture with a given mass of black product in a given quantity of aromatic solvent is started with and a paraffinic solvent is added in successive increments. The flocculation threshold is determined (in particular by a method using an IR probe) and the dilution rate and the aromaticity associated with the mixture analyzed are recorded. A first point, identified by the point P1 on the graph (FIG. 1) is obtained. The operation is started again, with a starting product which is initially less diluted in the aromatic solvent. Another measurement is then obtained marked by the point P2. With the two points P1 and P2 it is then possible to plot the straight line passing through these points and to obtain limit values (1−Pa) on the ordinates axis (limit aromaticity or infinite dilution rate) and 1/(P−1) on the abscissae axis (nil aromaticity). It then becomes possible to obtain the values of P and Pa then of Po through calculation.

This technique, which cannot refer to a standardized method as it does not currently exist, and which consists in the construction of a precipitation curve, using at least two measurement results, in order to then determine the values of the limit and nil aromaticities, is the one generally followed in the invention. The masses, the volumes and the products used are perfectly common in the state of the art of this type of analysis.

Figure 2:
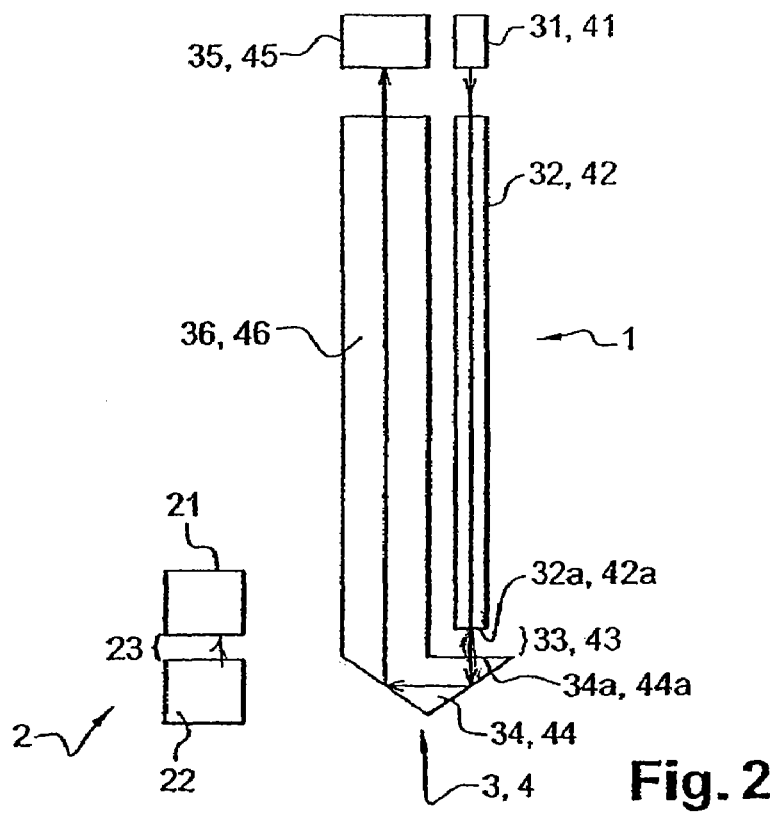
FIG. 2 is a diagrammatic representation of a device according to a first embodiment of the invention.

With reference to FIG. 2, the device (1) according to the invention comprises one the one hand a probe (2) operating in direct transmission, and on the other hand, at least one probe, preferably two probes (3, 4), operating in indirect transmission by reflection. The probe (2) comprises an emitter (21) and a receiver (22), creating between them a detection zone (23), here for example of 0.5 mm. The emitter is a standard IR emitter, as is the receiver. The useful diameter of the emitter is in particular of 0.6-0.7 mm. This probe (2) is of a type common in the art; it corresponds to a probe commonly used in the IR method proposed by Texaco Belgium SA. The probes (3, 4) are of a type which is new in the art. They are based on a principle of transmission by reflection, using a waveguide. For example the probe (3) comprises a first NIR emitter (31) coupled with a waveguide (32), for example a glass cylinder. This glass cylinder can have a diameter for example of 3 to 5 mm, typically approximately 4 mm. This waveguide transmits the light at the level of a first detection zone (33) which is situated between the lower end (32a) of the waveguide (32) and the aperture (34a) of a second waveguide (36). Two reflecting mirrors (34) are arranged as close as possible to this aperture and in such a way that they return the radiation to the receiver (35), by means of the waveguide (36), preferably made of glass. Preferably, the mirrors (34) and the return waveguide (36) are formed in one piece, and the system consequently has the general shape of a J. The appreciably lengthened part of the waveguide (36) preferably has a crescent shape for the sake of the compactness of the equipment (the plane face is preferably covered with black insulating material in order to prevent interference by the waveguide (32)). The reflecting planes of the mirrors are generally made of glass and are covered with a material suitable for the mirror function. For example, the probe (4) also comprises a first NIR emitter (41) coupled with a waveguide (42), similar and preferably identical to the waveguide (32) described above. This waveguide emits at the level of a second detection zone (43) which is situated between the lower end (42a) of the waveguide (42) and the aperture (44a) of a second waveguide (46). The reflecting mirrors (44) operate in the same way as above and the radiation is returned to a receiver (45), by means of the waveguide (46), similar to that already described above. Here, in a manner which is also preferred, the mirrors (44) and the return waveguide (46) are formed in one piece. Particularly preferably, the mirrors (34, 44) and waveguides (36,46) are combined as mirrors and waveguides in one unit, as are the receivers (35) and (45). An improved compactness of the system is thus obtained. The measurement zones (33) and (43) have distinct dimensions which can vary, for example, from 1 to 5 mm, and preferably from 1 to 3 mm, respectively Thus, each probe (3,4) carries out measurements under different conditions of optical path length. It is possible to place the emitters (31, (41) and receivers (35-45) not in contact with the fluid to be tested, which prevents any contamination. The fact of having waveguides with a light-reflecting operating mode is particularly useful for products containing few asphaltenes. In the standard techniques, the probes and emitters are face to face (which requires a practically complete immersion of at least the receiver in the product to be analyzed) and have a relatively small useful area (diameter of the emitters/receivers of the order of 0.7 mm), which means that for these types of products there is a risk of dispersion of the measurements due to saturation phenomena related to the receiver. The use of a waveguide with a larger surface and cross-section (in particular more than 10 times the cross-section of a standard probe) makes it possible to overcome this drawback by encouraging the absorption of light all along the optical path length.

The operation of the device according to the invention is described below.

The probes (2, 3, 4) of the device according to the invention are dipped in the medium to be analyzed and the apparatus automatically determines the probe to be used as a function of the results of preliminary measurements of optical transmission on the product to be analyzed, before the addition of the paraffinic solvent, i.e. before flocculation. These preliminary measurements are controlled automatically by a computer program which is predetermined during construction of said apparatus. Incremental additions of paraffinic solvent are then carried out and the drop in transmission corresponding to flocculation of the asphaltenes is recorded. This determination is carried out by means of standard techniques, for example, by measurement of the absorption peak.

According to an advantageous embodiment, the integrated character of the device according to the invention which combines the three probes is used. Firstly, the apparatus selects the probe (4) and then sends an increasingly strong signal, for example of 0 to 100 mA. If no signal is detected at the receiver, this means that the product is too absorbent and then probe (3) is used which operates with a smaller detection zone (1 mm compared to 3 mm for example). The operation is then started again. If at this stage there is still no signal detected, the product is still too absorbent and there is then a switch to probe (1) (small detection zone, 0.5 mm). Measurements will then be carried out with this probe. If, at a point of the method as the emission increases in strength, a signal is noticed, the probe will be kept which is then chosen for measurement of the current sample. When a signal is detected, the emission value of the emitter is set to the threshold value of the signal. In this way, it is possible to choose the probe "in situ", which affords the operator a significant time saving.

Moreover, the integration of 3 probes in the same device makes it possible to obtain a possible spectral application range for the measurements which is very wide. The device according to the invention is suitable for the determination of the values of P, Pa and Po for all residues and fuel oil types and has practically no limits in terms of the nature of the medium to be tested. Since the probes are integrated in one and the same device, it is possible to carry out several measurements in less time, which at least makes it possible to carry out 3 measurements and therefore to obtain 3 points of the curve and thus a good repeatability of the measurements for P, Pa and Po. Finally, the method of determination according to the invention can be carried out at ambient temperature and requires no beating during measurement.

Generally, the aromatic solvent/paraffinic solvent pair used in the invention is the toluene/n-heptane pair.

The different constituent elements of the device according to the invention are available from the ROFA company.

EXAMPLES

The following examples illustrate the invention without limiting it.

Example 1

Comparative measurements were carried out on 8 samples of different black products for which the P, Pa values were measured and the Po value was calculated, on the one hand with a method using the probes proposed by Texaco Belgium SA ("Measurement method A" in Table 1 below) and on the other hand with the device and the method according to the present invention ("Measurement method B").

In this example, the black products referenced PN1 to PN8 correspond to:

PN1 and PN2/Residues of desulphuration of an atmospheric residue;

PN3 and PN4/Fuel oils;

PN5 and PN6/Visbroken residues under vacuum;

PN7/Charge of a visbreaking unit (Residue under vacuum+ 20% atmospheric residue);

PN8/Visbroken residue under vacuum

TABLE 1

Comparison of the results of the P and Pa measurements, and the calculation of Po, with the Texaco probes (Measurement method A) and the device and method according to the invention (Measurement method B)

| | Measurement method A | | | Measurement method B | | |
|---|---|---|---|---|---|---|
| Products | P | Pa | Po | P | Pa | Po |
| PN1 | Undetectable | | | 2.49 | 0.62 | 0.95 |
| PN2 | 1.92 | 0.71 | 0.57 | 1.92 | 0.71 | 0.57 |
| PN3 | 1.52 | 0.31 | 1.05 | 1.55 | 0.29 | 1.09 |
| PN4 | 3.6 | 0.75 | 0.91 | 3.43 | 0.76 | 0.83 |
| PN5 | 1.75 | 0.56 | 0.77 | 1.92 | 0.56 | 0.84 |
| PN6 | 1.52 | 0.56 | 0.67 | 1.54 | 0.56 | 0.68 |
| PN7 | Undetectable | | | 4.22 | 0.82 | 0.77 |
| PN8 | 1.89 | 0.30 | 1.33 | 1.88 | 0.32 | 1.29 |

In this table, it can be seen that with the device and method according to the invention, it is easier to obtain the measurement of the flocculation threshold of a clear product (PN1) and also of a stable product (PN7) which is made clear by a significant dilution. These two products could not initially be measured in terms of P, Pa and therefore of Po with the standard manual method using the Texaco probes. For each of the 8 measurements, the correlation coefficient $R^2$ of the precipitation curve (aromaticity as a function of the reciprocal of the dilution) constructed with 3 points (P1, P2 and P3) varies from 0,976 to 1,000.

Moreover, automation of the analysis, including the choice of the probe most suited to the measurement, makes it possible to carry out the complete analysis in less than one hour.

Example 2

In order to compare the repeatability values obtained with the measurements of P, Pa then of calculated Po, which can be obtained by the manual method using the Texaco probes (Measurement methods A) and the automated method the device and the method of which are the subject of the present invention (Measurement method B), 3 samples PN2, PN3 and PN8 were chosen from the corpus defined in Example 1 above.

The results for 8 different measurements, with the 2 methods, on each of these 3 samples are shown respectively in Tables 2, 3 and 4 below. The average values calculated, as well as the standard deviations and the repeatabilities are shown in these same tables.

TABLE 2

Measurement of the repeatabilities of the values P, Pa and Po on the sample PN2 obtained with the Texaco probes (Measurement method A) and the device and method according to the invention (Measurement method B)

| Number of | PN2 | | | | | |
|---|---|---|---|---|---|---|
| | Measurement method A | | | Measurement method B | | |
| analyses | P | Pa | Po | P | Pa | Po |
| 1 | 1.96 | 0.71 | 0.57 | 1.92 | 0.71 | 0.56 |
| 2 | 1.99 | 0.70 | 0.60 | 1.92 | 0.71 | 0.57 |
| 3 | 1.88 | 0.73 | 0.51 | 1.89 | 0.71 | 0.54 |
| 4 | 1.80 | 0.68 | 0.58 | 1.92 | 0.71 | 0.55 |
| 5 | 2.00 | 0.67 | 0.66 | 1.96 | 0.71 | 0.57 |
| 6 | 1.85 | 0.72 | 0.52 | 1.88 | 0.71 | 0.54 |
| 7 | 1.98 | 0.76 | 0.47 | 1.90 | 0.71 | 0.55 |
| 8 | 1.90 | 0.70 | 0.57 | 1.91 | 0.71 | 0.56 |
| Average | 1.92 | 0.71 | 0.56 | 1.91 | 0.71 | 0.56 |
| Standard deviation | 0.07 | 0.03 | 0.06 | 0.02 | 0.00 | 0.01 |
| Repeatability | 0.20 | 0.08 | 0.17 | 0.06 | 0.00 | 0.03 |

TABLE 3

Measurement of the repeatabilities of the values P, Pa and Po on the sample PN3 obtained with the Texaco probes (Measurement method A) and the device and method according to the invention (Measurement method B)

| Number of | PN3 | | | | | |
|---|---|---|---|---|---|---|
| | Measurement method A | | | Measurement method B | | |
| analyses | P | Pa | Po | P | Pa | Po |
| 1 | 1.42 | 0.36 | 0.91 | 1.54 | 0.32 | 1.05 |
| 2 | 1.44 | 0.33 | 0.96 | 1.58 | 0.30 | 1.10 |
| 3 | 1.52 | 0.29 | 1.07 | 1.56 | 0.30 | 1.09 |
| 4 | 1.40 | 0.37 | 0.88 | 1.53 | 0.32 | 1.04 |
| 5 | 1.55 | 0.30 | 1.08 | 1.54 | 0.31 | 1.07 |
| 6 | 1.48 | 0.35 | 0.96 | 1.52 | 0.31 | 1.05 |
| 7 | 1.50 | 0.36 | 0.96 | 1.51 | 0.32 | 1.03 |
| 8 | 1.53 | 0.30 | 1.07 | 1.54 | 0.32 | 1.05 |
| Average | 1.48 | 0.33 | 0.99 | 1.54 | 0.31 | 1.06 |
| Standard deviation | 0.05 | 0.03 | 0.08 | 0.02 | 0.01 | 0.02 |
| Repeatability | 0.14 | 0.08 | 0.22 | 0.06 | 0.03 | 0.06 |

TABLE 4

Measurement of the repeatabilities of the values P, Pa and Po on the sample PN8 obtained with the Texaco probes (Measurement method A) and the device and method according to the invention (Measurement method B)

| Number of | PN8 | | | | | |
|---|---|---|---|---|---|---|
| | Measurement method A | | | Measurement method B | | |
| analyses | P | Pa | Po | P | Pa | Po |
| 1 | 1.89 | 0.30 | 1.32 | 1.84 | 0.30 | 1.29 |
| 2 | 1.80 | 0.33 | 1.20 | 1.88 | 0.32 | 1.29 |
| 3 | 1.92 | 0.31 | 1.32 | 1.85 | 0.30 | 1.30 |
| 4 | 1.78 | 0.34 | 1.17 | 1.83 | 0.32 | 1.25 |
| 5 | 1.85 | 0.28 | 1.33 | 1.86 | 0.32 | 1.26 |
| 6 | 1.82 | 0.28 | 1.24 | 1.83 | 0.33 | 1.23 |
| 7 | 1.92 | 0.34 | 1.27 | 1.84 | 0.33 | 1.23 |
| 8 | 1.90 | 0.29 | 1.35 | 1.88 | 0.32 | 1.28 |
| Average | 1.86 | 0.31 | 1.28 | 1.85 | 0.32 | 1.27 |
| Standard deviation | 0.06 | 0.02 | 0.07 | 0.02 | 0.01 | 0.03 |
| Repeatability | 0.17 | 0.06 | 0.20 | 0.06 | 0.03 | 0.08 |

It can be seen in Tables 2, 3 and 4 that the average values obtained with the 2 measurement methods are more or less identical and above all that the values of the standard deviations and the repeatabilities are smaller by a factor of approximately 3 when the measurement method uses the device for detecting the flocculation threshold and the related method according to the present invention (with a complete automation of the measurement method in this case).

The invention claimed is:

1. Method for measuring the flocculation threshold of a colloidal medium comprising asphaltenes by the addition in stages of apolar solvent comprising the following stages:
   (i) at least two probes are introduced into the medium, which probes operate by optical transmission at the level of detection zones with distinct dimensions;
   (ii) which of the at least two probes is suited for the measurement is determined by determination of the transmission threshold of the medium before addition of apolar solvent; and
   (iii) using the probe suited for measurement determined at step (ii) flocculation is determined after addition of the quantity of the apolar solvent necessary for flocculation at substantially ambient temperature,
   wherein the at least two probes are comprised in a device for measuring light in a medium by inserting the at least two probes into said medium, wherein each of the at least two probes comprises an emitter connected to a first waveguide emitting at the level of a detection zone a light beam directly onto said zone, and a second waveguide receiving perpendicular to its aperture said light beam sent back to a receiver for analysis; said second waveguide containing at least one reflecting mirror reflecting the light beam by reflection, situated downstream of said detection zone; and wherein each of the at least two probes operates at the level of detection zones of the medium with distinct dimensions.

2. Method according to claim 1, in which each of the at least two probes emits in the NIR range and the occurrence of flocculation is determined by determination of the absorption peak.

3. Method for determining the stability of a mixture comprising asphaltenes by successively implementing at least twice the method according to claim 1 on a medium containing the mixture and a given quantity of aromatic solvent, at different dilution rates.

4. Method according to claim 3, in which the aromatic solvent is toluene and the apolar solvent is n-heptane.

5. Method according to claim 1, in which the light is constituted by wavelengths belonging to the spectral range of the near infrared or to the spectral range of the infrared.

6. Method according to claim 1, wherein each of the at least two probes probes is operating in indirect transmission by reflection.

7. Method according to claim 1, wherein said device further comprises at least one probe operating in direct transmission.

8. Method according to claim 1, wherein the reflecting mirrors are adapted to operate at 180°.

9. Method according to claim 1, wherein the reflecting mirrors and the second waveguide are integrated in a single piece.

10. Method according to claim 1, wherein the device comprises two of the at least two probes wherein the second waveguides of the two of the at least two probes are merged.

11. Method according to claim 1, wherein the first and second waveguides are made of glass.

12. Method according to claim 1, wherein the device comprises a probe adapted to operate in indirect transmission by reflection and at the level of a detection zone of the medium the dimension of which is variable.

13. Method according to claim 1, wherein the device comprises a first probe in direct transmission and adapted to operate at the level of a first detection zone of the medium; and two probes adapted to operate at the level of detection zones of the medium with distinct dimensions, the zones of the first probe and the two probes having increasing dimensions, the detection zone of the first probe being adapted to operate in direct transmission having the smallest dimension.

14. Method according to claim 1, wherein said detection zones vary from 1 to 5 mm.

15. The method of claim 1, wherein:
the determination of a transmission threshold comprises sending an increasingly strong signal to the emitter of one of the at least two probes until a signal is received at the receiver of the one of the at least two probes;
based on the determined transmission threshold, setting an emission value of the emitter of that one of the at least two probes for use in step (iii) as the probe suited for measurement determined at step (ii).

16. A method for measurement of a flocculation threshold of a colloidal medium comprising asphaltenes, the method comprising:
introducing at least two probes into the colloidal medium, each said probe having a detection zone through which light from an emitter is passed and received by a receiver, wherein the detection zone of each said probe has a level of detection zone with a dimension distinct from other of said probes;
with said probes inserted into the colloidal medium, choosing one of said probes for making the measurement, the choosing comprising:
(i) sending an increasingly strong input signal to the emitter of at least the one of said probes until the input signal reaches a threshold value at which a signal is noticed at the receiver of the one of said probes; and
(ii) selecting the one of said probes as a chosen probe for making the measurement;
setting the emitter of the chosen probe to operate at an emission value corresponding with the threshold value; and
with the emitter of the chosen probe operating at the emission value, using the chosen probe to determine the flocculation threshold of the colloidal medium after addition of a quantity of apolar solvent to cause flocculation.

\* \* \* \* \*